US006501979B1

(12) United States Patent
Manning et al.

(10) Patent No.: US 6,501,979 B1
(45) Date of Patent: Dec. 31, 2002

(54) METHODS AND DEVICES FOR COMBINED ECG AND PPU CONTROLLED MAGNETIC RESONANCE IMAGING

(75) Inventors: Warren J. Manning, Boston; Rene M. Botnar; Matthias Stuber, both of Brookline, all of MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/521,714

(22) Filed: Mar. 9, 2000

(51) Int. Cl.[7] .............................................. A61B 5/055
(52) U.S. Cl. ...................................... 600/413; 600/428
(58) Field of Search ................................. 600/413, 425, 600/428, 436, 407, 419; 324/306, 307, 309

(56) References Cited

U.S. PATENT DOCUMENTS

| | | | |
|---|---|---|---|
| 4,855,910 A | 8/1989 | Bohning | 364/413.13 |
| 5,000,182 A | 3/1991 | Hinks | 128/653 A |
| 5,329,925 A * | 7/1994 | NessAiver | 324/306 |
| 5,477,144 A * | 12/1995 | Rogers, Jr. | 324/300 |
| 5,492,123 A * | 2/1996 | Edelman | 600/410 |
| 5,526,813 A | 6/1996 | Yoshida | 128/653.2 |
| 5,692,508 A | 12/1997 | Simonetti et al. | 128/653.3 |
| 5,897,496 A * | 4/1999 | Watanabe | 600/413 |

FOREIGN PATENT DOCUMENTS

| | | | |
|---|---|---|---|
| JP | 09220211 A | 8/1997 | A61B/5/055 |
| WO | 99/04688 | 2/1999 | A61B/5/0456 |

OTHER PUBLICATIONS

"An ECG Trigger Module for the Acquisition of Cardiac MR Images" by R. Deklerck et al., Computers in Cardiology 1994, pp. 533–536.

C. Clark et al, "Magnetic Resonance Diffusion Imaging of the Human Cervical Spinal Cord In Vivo", Magnetic Resnance In Medicine, Wiley, USA, vol. 41, No. 6, Jun. 1999, pp. 1269–1273, XP002181420.

H. Bakema et al, "Thorax Radiography with E.C.G. and Respiration Control", Medical and Biological Engineering, vol. 13, No. 4, Jul. 1975, pp. 588–591, XP002181421.

* cited by examiner

*Primary Examiner*—Marvin M. Lateef
*Assistant Examiner*—Eleni Mantis Mercader
(74) *Attorney, Agent, or Firm*—John Vodopia

(57) ABSTRACT

This invention relates to methods and apparatus for medical imaging of parts of a patient in which imaging data acquisition is gated by a combination of electrocardiogram (ECG) and peripheral pulse (PPU) signals from the patient. The methods of the invention include obtaining ECG signals from a patient in a medical imaging apparatus, obtaining PPU signals from the patient, providing one or more synchronization signals in dependence on both the ECG signals and the PPU signals, wherein the synchronization signals indicate occurrences of pre-determined phases of the cyclic movements of the heart only if the PPU signals also indicate that the determined heart phase is physiologically possible, and controlling the medical imaging apparatus in dependence on the synchronization signals to collect imaging data synchronized with cyclic movements of the heart from the patient in the examination zone and to reconstruct a medical image of a part of the patient from the collected imaging data. The medical imaging apparatus of the invention includes such units in addition to the imaging units as are necessary from the practice of the methods of the invention. This invention is preferably applied to magnetic resonance imaging and to computed tomographic x-ray imaging.

20 Claims, 6 Drawing Sheets

METHODS AND DEVICES FOR COMBINED ECG AND PPU CONTROLLED MAGNETIC RESONANCE IMAGING

BACKGROUND OF THE INVENTION

1. Field of the Invention

The present invention relates to methods and systems for medical imaging of parts of a patient in which acquisition of data by a medical imaging apparatus for image reconstruction is gated by a combination of electrocardiogram (ECG) and peripheral pulse (PPU) signals from the patient.

2. Description of the Related Art

Many organs and regions of the body of a patient are affected by cardiac and respiratory motions, including, for example, not only the heart, the lungs, and vessels throughout the body, but also abdominal organs, especially upper abdominal organs, and intracranial structures. For the medical imaging of such affected organs, it is often useful, or even necessary, to take these motions into account. On the one hand, in the case of those imaging modalities, such as a conventional x-ray imaging, in which a single image is acquired in a short exposure (for example, a few milliseconds (msec) or less), it is often useful for images to be acquired at known and pre-determined phases of cardiac or respiratory motions.

However, on the other hand, in the case of those imaging modalities which reconstruct a recognizable image from imaging data acquired over a period of time (for example, 100 msec. or more), it is often necessary to take body motion into account in order to avoid motion artifacts that degrade reconstructed images and render them less useful clinically. Currently, important modalities of this nature include magnetic resonance (MR) imaging, computer tomographic (CT) x-ray imaging, and nuclear imaging of particles emitted by radioactive tracers administered to a patient. For many cardiac, vascular, neurologic, and other imaging examinations using such modalities, synchronization of imaging data collection sequences to the intrinsic motion of the heart is crucial to obtain high-quality images without motion artifacts.

For cardiac synchronization of medical imaging data collection, triggering data collection by features recognized in the electrocardiogram (ECG) signal or in the peripheral pulse (PPU) signal from nearly any artery can be utilized. PPU signals, in comparison to ECG signals, are always delayed with respect to the QRS complex of the ECG signal (signifying the onset of ventricular systole), and have a temporal frequency spectrum with significantly lower frequency components. The variable delay can be up to 100–200 msec. or more. Therefore, triggering with ECG signals is generally preferred to achieve triggering that is temporally more precisely defined in time and to enable data collection during early ventricular systole.

However, important medical imaging modalities often introduce noise and distortions into ECG signals measured from a patient during imaging examinations. These noise and distortions are due to various kinds of electromagnetic interference inherently generated during examination by such modalities. In the case of CT and nuclear imaging, electrical interference may be induced in the patient or in affixed ECG leads, and therefore, into resulting ECG signals, either directly from the imaging apparatus itself or secondarily by radiation used in the imaging.

In the case of MR imaging, switched magnetic field gradients, RF pulses, and hydrodynamic flows of blood containing charged ions in the strong static magnetic field present in an MR apparatus induce voltage gradients in a patient that in turn introduce noise and distortions into ECG signals. Since blood flow effects are enhanced during systole, when the blood flows in the aorta and other vessels are increased, introduced ECG artifacts are maximum during ventricular systole. Such artifacts hamper R-wave detection and, thus, successful synchronization of imaging data collection.

For example, FIG. 2A illustrates two ECG signals from a healthy volunteer. ECG 80 is recorded in an MR apparatus but without the presence of the static main magnetic field. ECG 81 is recorded in the MR apparatus in the presence of a static field of, for example, 1.5 Tesla (T). Second ECG 81, recorded in the presence of the static magnetic field, contains several additional signal peaks compared to first ECG 80, which can lead to erroneous interpretations of the ECG, for example, being recognized as non-physiological, false R-waves.

A method and apparatus that attempts to improve ECG triggering is known from U.S. Pat. No. 5,526,813. In this known method, erroneous determination of ECG features is reduced by filtering and signal processing prior to using the signal for triggering imaging data collection. However, a drawback of this known method is that the filtering and signal processing of the ECG data can be complicated and unreliable, and as a result erroneous triggering of imaging data acquisition may still occur even though the ECG signals have been filtered and processed. Another method and apparatus that also attempts to improve ECG triggering is known from International Application no. PCT/IB98/01062. According to the latter known method, information from a vector ECG (VCG) signal is used to improve recognition of ECG signal features compared to their recognition in a scalar ECG. However, measurement of a vector electrocardiogram signal is also subject to inherent noise and distortions generated by the imaging modalities, and its analysis can also be complex, difficult, and unreliable.

What is needed, therefore, are simple and reliable methods and apparatus for accurately and reliably triggering data acquisition for medical image reconstruction at fixed times with respect to the cardiac cycle.

Citation of a reference herein, or throughout this specification, is not to be construed as an admission that such reference is prior art to the Applicants' invention of the invention subsequently claimed.

SUMMARY OF THE INVENTION

The objects of the present invention are to provide methods and apparatus which overcome the above identified problems in, and satisfy the needs of, the current medical imaging art.

As used herein, it is to be understood that a "medical imaging modality" is any imaging modality that acquires imaging data by a process that can be disturbed by body motions, and, therefore, that advantageously takes heart motions into account when imaging organs that are directly or indirectly affected by such heart motions. This invention is most advantageously applied to those imaging modalities the practice of which generates noise and distortions of electrocardiogram (ECG) signals measured from a patient during imaging. Preferably, this invention is applied to magnetic resonance (MR) imaging, or to computer tomographic (CT) x-ray imaging, or to nuclear medicine imaging.

Additionally, as used herein, it is to be understood that "ECG signals" means any representation of the electrical activity of the heart. It includes conventional scalar representations where the time courses of single voltages measured between established positions on the patient are displayed. In these representations, the QRS complex has its well-known form, e.g., as schematically represented by signal 80 in FIG. 2A. It also includes vector electrocardiogram (VCG) representations, where the time course of the net electrical polarization vector of the heart is displayed in various projections. In these representations, the QRS complex is seen as a loop elongated along one direction. Finally, it is to be understood that "PPU signal" means any representation of the pulsatile flow of blood in an artery. It can be non-invasively measured, for example, by an oximeter, or invasively measured, for example, by arterial pressure, or by other means.

Generally, the objects of this invention are achieved by medical imaging methods according to which information from both ECG signals and from PPU signals are considered together in order to generate reliable synchronization signals for triggering imaging data collection in a medical imaging apparatus. The synchronization signals represent occurrences of pre-determined phases of cardiac motion so that the imaging data collection can be synchronized with the actual, physiologic, cyclic movements of the heart and with resulting blood flows. These objects are also achieved by medical imaging apparatus that, in addition to its conventional imaging means, includes further functional units necessary to practice the methods of medical imaging methods of this invention, such units as, for example, an ECG unit, and PPU unit and a synchronization unit.

Although, this invention is described herein primarily in its preferred embodiment directed to MR imaging and utilizing scalar ECG signal representations, it will be understood that this invention is not so limited. For example, it is equally applicable use of VCG signals, to CT imaging gated and to other imaging modalities. It is intended that these other embodiments apparent to one of skill in the art from the following drawing and description are also covered by the appended claims.

In detail, the objects of this invention are achieved by the following embodiments. In a first embodiment, the general methods of the invention include obtaining ECG signals representing the electrocardiogram of a patient placed in an examination zone of a medical imaging apparatus which collects medical imaging data for reconstruction of a medical image, obtaining PPU signals representing occurrences of peripheral pulses in the patient, providing one or more synchronization signals representing occurrences of one or more pre-determined phases of the cyclic movements of the heart, wherein the synchronization signals are provided in dependence on both the ECG signals and on the PPU signals, and controlling the medical imaging apparatus in dependence on the one or more synchronization signals in order to collect imaging data synchronized with cyclic movements of the heart from a part of the patient in the examination zone and to reconstruct a medical image of a part of the patient from the collected imaging data with reduced or absent motion artifacts.

In various aspects of the first embodiment, the part of the patient imaged includes cardiac structures, or intracranial structures, or vascular structures; the medical imaging apparatus is a magnetic resonance apparatus or a computed tomography x-ray apparatus; and the ECG signals include scalar ECG signals or vector ECG signals. In a further aspect, the synchronization signals are provided only if the PPU signals indicate that the pre-determined cardiac phases are physiologically possible. In this aspect, the general methods include determining, first, PPU-derived information from the PPU signals, wherein the PPU-derived information indicates time intervals within which the predetermined cardiac phases are physiologically more probable or less probable, and recognizing, second, the pre-determined cardiac phases in the ECG signal, wherein the recognizing is responsive to the probability or improbability of the pre-determined cardiac phases indicated by the PPU-derived information. Further, the PPU-derived information preferably indicates black-out intervals within which the pre-determined cardiac phases cannot occur, and within which the pre-determined cardiac phases are not recognized; or the PPU-derived information indicates window intervals only within which the predetermined cardiac phases can occur, and within which the pre-determined cardiac phases are recognized. Also, the provided synchronization signals preferably further include verification-type signals which indicate whether or not a previous synchronization signal represents a physiologic cardiac phase, and wherein the medical imaging apparatus is controlled to not use for image reconstruction imaging data collected in response to non-physiologic synchronization signals.

In further aspects of the first embodiment, the provided synchronization signals are R-wave-type synchronization signals that signal occurrences of R-waves in the ECG signals, and wherein the step of controlling collects imaging data in a pre-determined temporal relation to R-wave-type signals. Optionally, the pre-determined temporal relation is such that imaging data is collected during cardiac diastole. In one preferable alternative, from the PPU signal, black-out intervals are determined within which physiologic R-wave cannot occur in the ECG signals, and the R-wave-type synchronization signals are not provided during black-out intervals. Where the PPU signal comprises PPU complexes having positive lobes indicating peripheral systolic blood flow, the black-out intervals comprise the duration of the positive lobes of PPU complexes. In another preferable alternative, from the PPU signal, window intervals are determined within which physiologic R-waves in the ECG signal must occur, and the R-wave-type synchronization signals are provided only during window intervals. Where the PPU signal comprises PPU complexes having positive lobes indicating peripheral systolic blood flow, each window interval comprises an interval which begins at a pre-determined duration after the end of a just previous QRS complex in the ECG signal, and which ends at the beginning of the positive lobe of an immediately next PPU complex.

In a second embodiment, the invention includes a magnetic resonance apparatus for acquiring images of a part of a patient placed in an examination zone of the MR apparatus, the apparatus comprising a main magnet system for generating a steady magnetic field in the examination zone, a gradient magnet system for generating temporary gradient magnetic fields in the examination zone, a radio frequency (RF) transmitter system for generating RF pulses in the examination zone, an RF receiver system for receiving MR signals from the examination zone, an ECG system for obtaining ECG signals representing the electrocardiogram of the patient, a peripheral pulse unit system for obtaining PPU signals representing occurrences of peripheral pulses in the patient, a reconstruction unit for reconstructing an image of the region of the patient from the received MR signals, a control unit responsive to one or more synchronization signals for generating control signals controlling the gradient magnet system, the RF transmitter system, the RF receiver system, and the reconstruction unit, wherein the synchronization signals represent occurrences of one or more pre-determined phases of the cyclic movements of the heart, and wherein the control signals cause acquisition of MR data for the reconstruction an image of a part of the patient, and a synchronization unit for providing the one or more synchronization in dependence on both the ECG signals and on the PPU signals in order to synchronize the acquisition of MR signals with cyclic movements of the heart.

In various aspects of the second embodiment, the synchronization unit of the MR apparatus further comprises means for determining, first, PPU-derived information from the PPU signals, wherein the PPU-derived information indicates time intervals within which the pre-determined cardiac phases are physiologically more probable or less probable, and means for recognizing, second, the pre-determined cardiac phases in the ECG signals, wherein the recognizing is responsive to the probability or improbability of the pre-determined cardiac phase indicated by the PPU-derived information. Preferably, the synchronization unit further comprises one or more programmable elements, and one or more memories for storing instructions for causing the synchronization to function for providing the synchronization signals in dependence on both the ECG signals and on the PPU signals.

In a third embodiment the invention includes a computed tomography (CT) x-ray apparatus for acquiring images of a part of a patient placed in an examination zone of the CT apparatus, the apparatus comprising a radiation source, a detector unit which is coupled to the radiation source, means for causing the radiation source and the detector unit to perform a rotational scanning motion about the patient in the examination zone during which scanning motion measuring data is acquired, an ECG system for obtaining ECG signals representing the electrocardiogram of the patient, a peripheral pulse unit system for obtaining PPU signals representing occurrences of peripheral pulses in the patient, a reconstruction unit for reconstructing the spatial distribution of the absorption within the patient from the measuring data acquired by the detector unit, and a control unit responsive to one or more synchronization signals for generating control signals controlling the radiation source, the detector unit, the means for causing a rotational scan, and the reconstruction unit, wherein the synchronization signals represent occurrences of one or more pre-determined phases of the cyclic movements of the heart, and wherein the control signals cause acquisition of measuring data for the reconstruction an image of a part of the patient, and a synchronization unit for providing the one or more synchronization signals in dependence on both the ECG signals and on the PPU signals in order to synchronize the acquisition of measuring data with cyclic movements of the heart.

In a fourth embodiment, the invention includes a computer readable media carrying encoded program instructions for causing a medical imaging apparatus to perform the method of claim 1.

BRIEF DESCRIPTION OF THE DRAWING

Other objects, features and advantages of the present invention will become apparent upon study of the following detailed description when taken in conjunction with the appended drawing, wherein.

DETAILED DESCRIPTION OF THE PREFERRED EMBODIMENTS

Figure 1A:
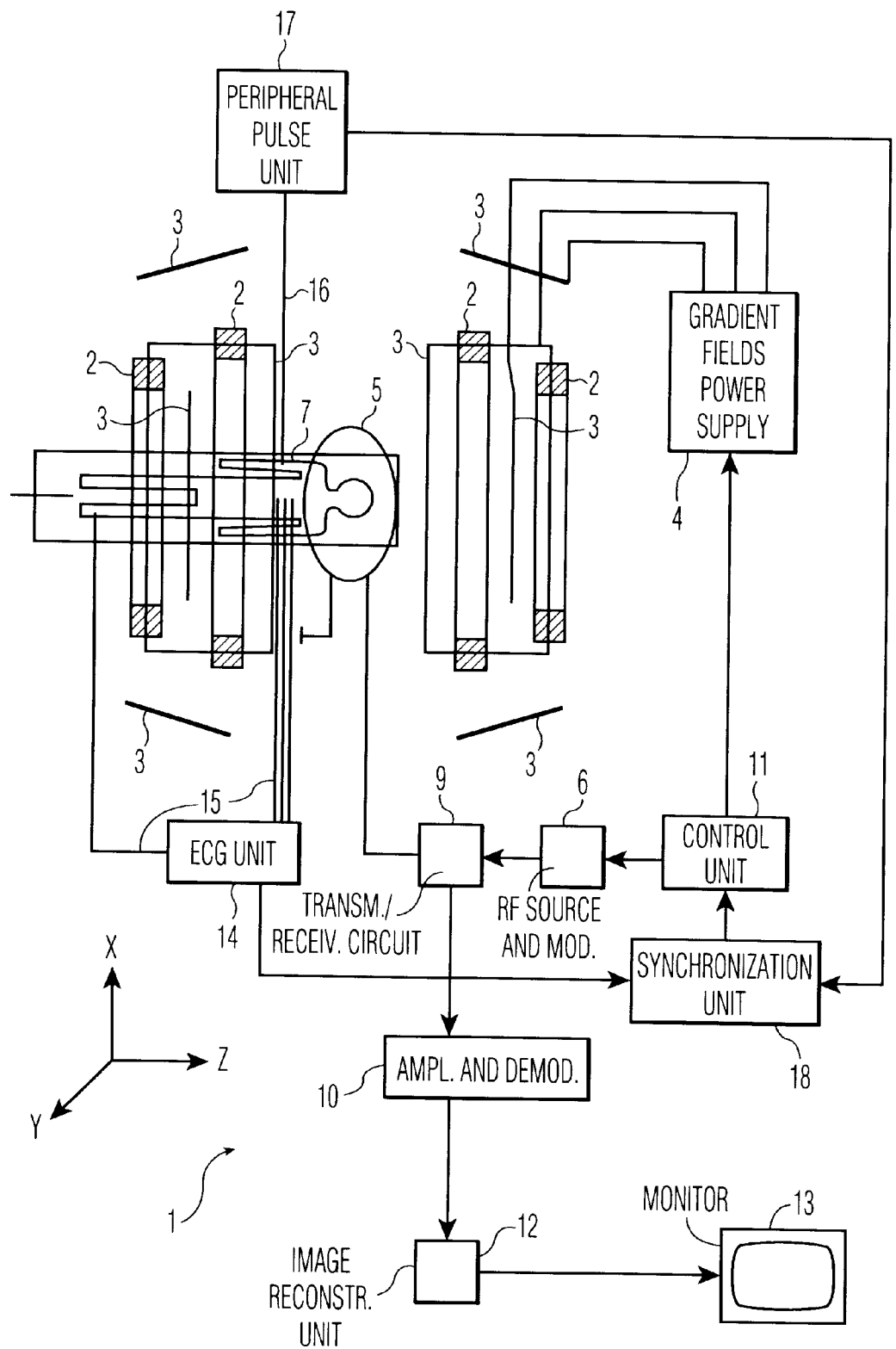
FIGS. 1A–B illustrates an exemplary embodiments of MR and CT apparatus, respectively, for practicing the present invention.

In the following, an exemplary embodiment of a medical imaging apparatus for practicing the methods of the present invention is first presented, followed by descriptions of preferred and alternative embodiments the methods of the present invention, including their exemplary implementation as computer hardware and/or software.

Although, this invention is described herein primarily in its preferred embodiment directed to MR imaging, and secondarily to CT imaging, both utilizing scalar ECG signal representations, it will be understood that this invention is not so limited. For example, it is equally applicable to CT imaging or nuclear imaging gated and controlled by a combination of VCG signals and PPU signals. It is intended that these other embodiments apparent to one of skill in the art from the drawing and following description are also covered by the appended claims.

An Exemplary MR-Apparatus of the Present Invention

FIG. 1A illustrates MR apparatus 1, which is an exemplary embodiment of an MR apparatus for practicing the present invention. MR apparatus 1 comprises main magnet system 2 for generating a steady magnetic field in an examination zone of the MR apparatus. The z-direction of the coordinate system illustrated corresponds to the direction of the steady magnetic field generated by magnet system 2. The MR apparatus also comprises gradient magnet system 3 for generating temporary magnetic fields directed in the z-direction but having gradients in the x, y or z direction, respectively. With this magnetic gradient system, magnetic gradient fields can also be generated that do not have directions coinciding with the main directions of the above coordinate system, but that can be inclined thereto. In this application, for ease of description, the directions x, y and z are used for the frequency encode, phase encode and slice-selection direction, respectively, while the temporary gradient fields having a gradient in the x-direction, the y-direction and the z-direction are referred to as read gradient, phase-encode gradient and slice-selection gradient, respectively. Power supply means 4 feed the gradient magnet system 3. Magnet systems 2 and 3 enclose an examination zone which is large enough to accommodate a part of object 7 to be examined, for example a part of a human patient.

The MR apparatus also comprises an RF transmitter system including RF transmitter coil 5, which generates RF pulses in the examination zone and is connected via transmitter/receiver circuit 9 to RF source and modulator 6. RE transmitter coil 5 is arranged around the part of body 7 in the examination zone. The MR apparatus also comprises an RE receiver system including an RF receiver coil which is connected via transmitter/receiver circuit 9 to signal amplification and demodulation unit 10. The receiver coil and the RF transmitter coil 5 may be one and the same coil.

The MR apparatus also comprises control unit 11 that generates MR imaging sequences comprising RF-pulses and temporary magnetic gradient fields by controlling the RF transmitter and receiver systems by means of modulator 6 and by controlling the gradient magnetic field system by means of power supply means 4. After excitation of nuclear spins in a part of the body placed within the examination space by magnetic gradient fields and RF pulses, the receiver coil receives an MR signal. The phase and amplitude derived therefrom are sampled and further processed in amplification and demodulation unit 10. Image reconstruction unit 12 processes the received MR signals to reconstruct an image. The reconstructed image is displayed, for example, on monitor 13. The control unit 11 also controls the image reconstruction unit 12.

Further, according to the present invention, the MR apparatus also comprises ECG unit 14 for obtaining ECG signals from the patient in the examination zone, peripheral pulse (PPU) unit 17 for obtaining ECG signals present in the patient in the examination zone, and synchronization unit 18, which receives the ECG and PPU signals and generates synchronization signals for the MR apparatus by combining information from both the received ECG and the received PPU signals. These additional unit are described below.

An Exemplary CT-Apparatus of the Present Invention

Figure 1B:
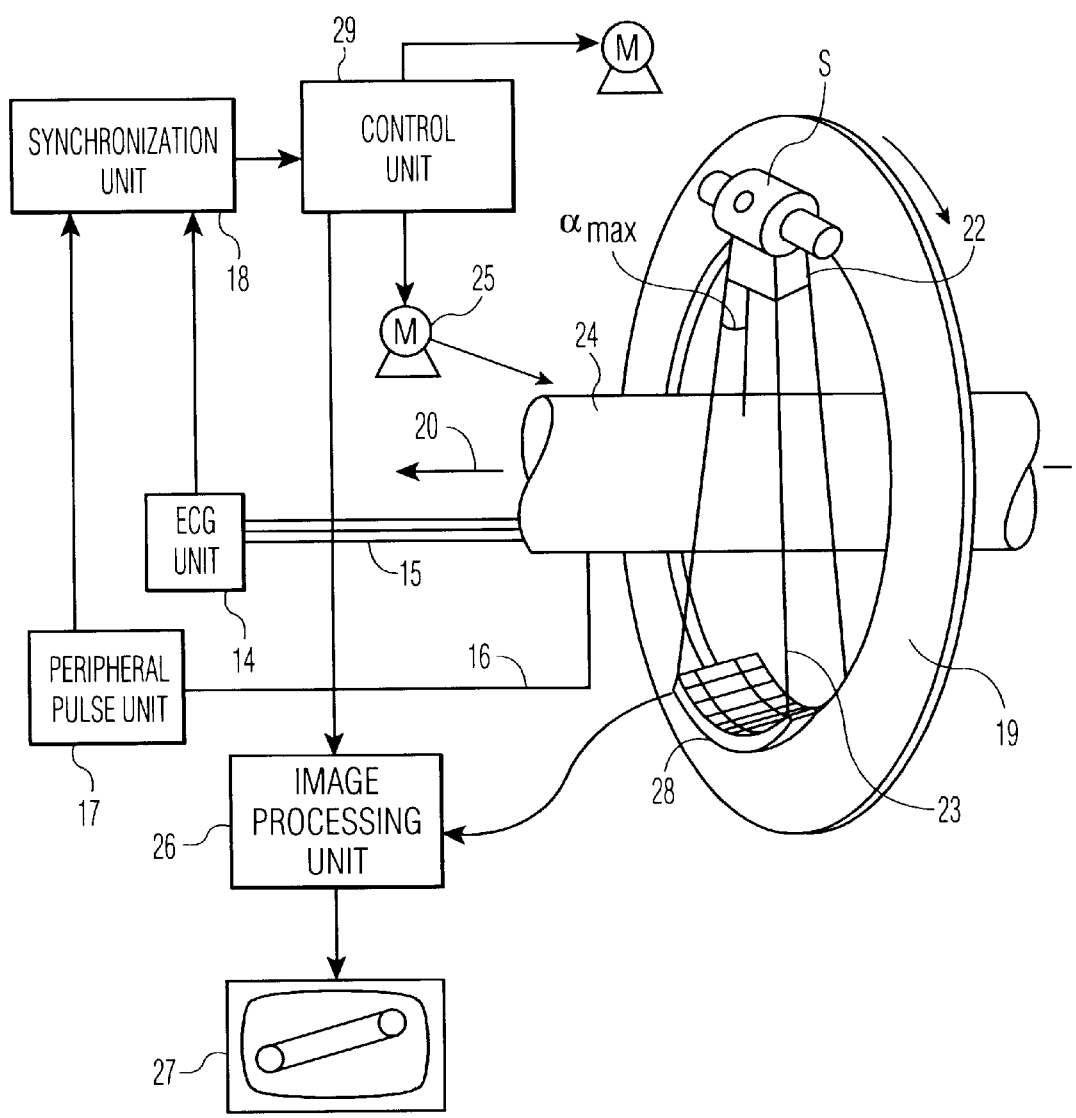

FIG. 1B illustrates a CT apparatus, which is an exemplary embodiment of a CT apparatus adequate for practicing the present invention. The illustrated CT apparatus comprises gantry 19 with connected radiation source S, for example an x-ray source, which can rotate about axis of rotation 20. Motor 21 is capable of rotating the gantry and the radiation source at an adjustable angular speed. Radiation source S is provided with collimator device 22 which forms radiation beam 23 into, alternately, a planar beam or into a cone-shaped beam with non-zero dimensions in two perpendicular directions. The angle of aperture, denoted by the reference $\alpha_{max}$, determines the diameter of patient which can be examined.

The CT apparatus also comprises detector unit 28, connected to gantry 19, on which is incident radiation beam 23 after having traversed schematically-illustrated patient 24, who may be accommodated on a patient table (not illustrated) in an examination zone (not illustrated). Motor 25 is capable of displacing the patient in the examination zone parallel to axis of rotation 20 at an adjustable linear speed. Detector unit 28, as illustrated here, comprises several detector rows, each of which comprises a plurality of detector elements. Alternately, the detector can comprise a single row of detector elements. Each detector element measures the intensity of a ray of radiation beam 23.

The illustrated CT apparatus also comprises control unit 29 for controlling the other units to acquire imaging data and to reconstruct a recognizable image. When the motors 21 and 25 are simultaneously activated by the control unit, radiation source S and detector unit 28 perform a helical scanning motion relative to the patient in the examination zone. Alternately, when motor 25 is inactive and motor 21 is activated by the control unit to rotate the gantry separately, the radiation source and detector unit perform a circular scanning motion. Under command of control unit 29, the source and the detector unit cooperate to acquire measuring data (i.e., x-ray intensity data) acquired during scanning motions are to apply the measuring data to image processing unit 26, which is, for example, a computer workstation. The image processing unit, or reconstruction unit, then reconstructs therefrom the absorption distribution in a part of the patient 24, and, for example, displays it on a monitor 27. Image reconstruction is by methods well-known for the separate cases of helical and circular scanning.

Further, according to the present invention, the CT apparatus also comprises ECG unit 14 for obtaining ECG signals from the patient in the examination zone, peripheral pulse (PPU) unit 17 for obtaining ECG signals present in the patient in the examination zone, and synchronization unit 18, which receives the ECG and PPU signals and generates synchronization signals for control unit 29 by combining information from both the received ECG and the received PPU signals. These additional unit are described next.

The ECG, PPU, and Synchronization Units of the Present Invention

Figure 2A:
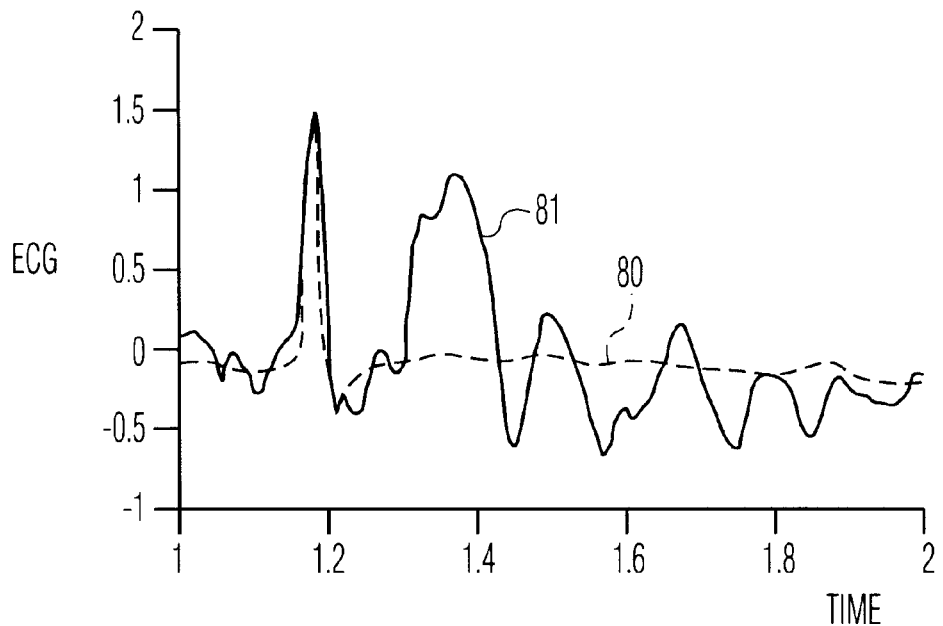
FIG. 2A illustrates a sample ECG signal from a patient placed in an MR apparatus.

Furthermore, according to the present invention, a medical imaging apparatus also comprises ECG unit 14 for obtaining ECG signals from the patient in the examination zone. In order to measure ECG signals, the ECG unit is connected to the patient in a known manner via electrodes 15 attached to the patient's body. See Fischer, 1999, Novel real-time R-wave detection algorithm for accurate gated magnetic resonance acquisitions, *Magnetic Resonance in Medicine* 42:361–70; and, generally, Marriott, 1972, Practical Electrocardiography, Williams & Wilkins Co., Boston, Mass. A measured ECG signal typically contains significant distortions, artifacts, and noise due to electromagnetic interference inherently generated by the imaging apparatus. For example, FIG. 2A compares ECG 80 signal measured in a quiescent MR apparatus with ECG signal 81 measured in the MR apparatus with the main magnetic fields present. Large artifacts are immediately apparent.

Also according to the present invention, the medical imaging apparatus comprises peripheral pulse (PPU) unit 17 for obtaining ECG signals present in the patient in the examination zone. In order to measure PPU signals, the PPU unit is connected to the patient in a known manner via sensor 16 placed in proximity to the patient's body. For example, the PPU signal is preferably measured by detecting changes in the response of a part of the patient's body, e.g., a finger or earlobe of the patient, to infrared (IR) radiation. The oxygenated hemoglobin in a pulse of arterial blood changes the IR optical properties of the patient's finger or earlobe in a measurable manner.

Finally, according to the present invention, the medical imaging apparatus comprises synchronization unit 18, which receives the ECG and PPU signals and generates synchronization signals by combining information from both the received ECG and the received PPU signals. In response to the synchronization signals, MR control unit 11 or CT control unit 29 is triggered to collect the MR imaging data or CT imaging data, respectively. By combining information from both signal sources in manners subsequently in detail next, image data collection can be synchronized with improved reliability to cyclic movements of the body due, for example, to the heart beat and blood flow of the patient within the imaging apparatus.

The Methods of the Present Invention

Figure 3:
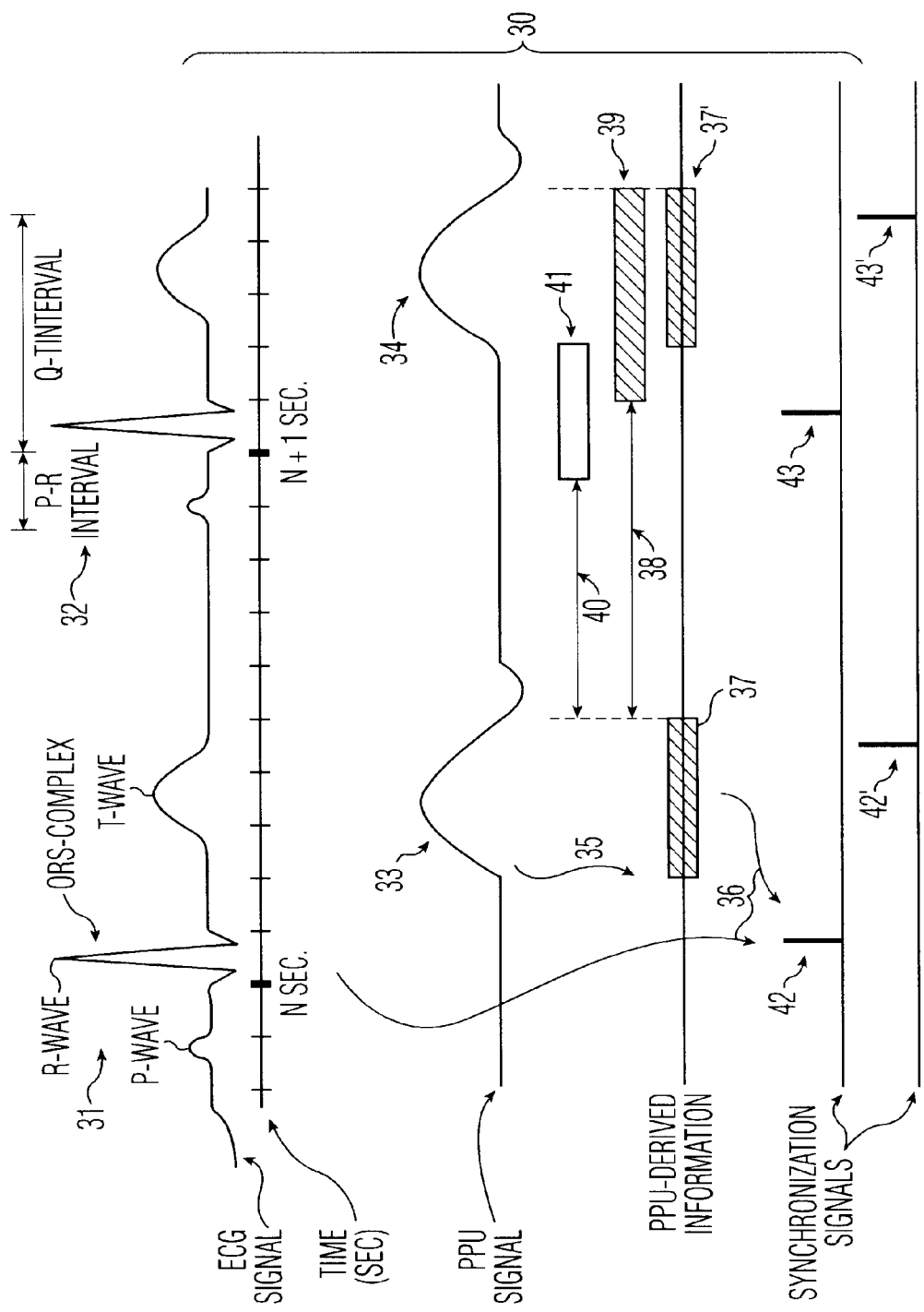
FIG. 3 illustrates input and output signals according to the present invention.
Figure 4A:
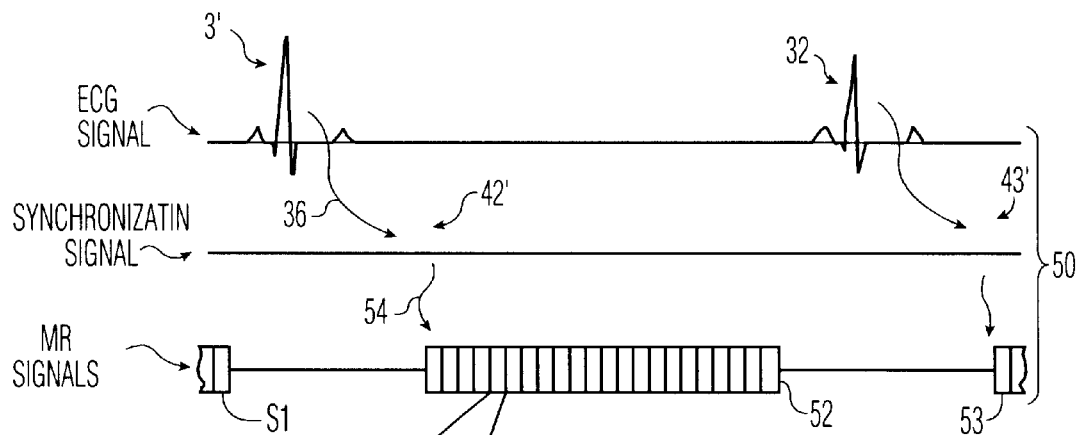
FIG. 4 illustrates MR signals generated in response to the synchronization signals.
Figure 4B:
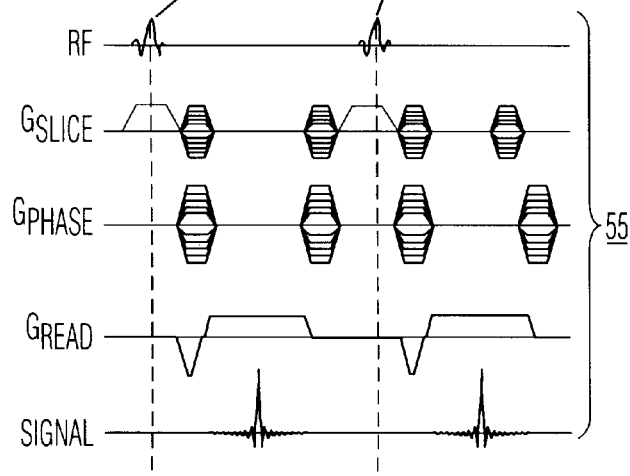

Next, with reference to FIGS. 3 and 4, preferred and alternative embodiments of the methods of the present invention are described. Generally, in comparison to the PPU signal, the ECG signal has more structure and provides the more detailed information about the various phases of the cardiac cycle, and, thereby, of blood flow in the body, but is more easily corrupted by noise, artifacts, and distortions when measured in a medical imaging apparatus. In contrast, the PPU signal, which unequivocally identifies peripheral arterial pulses, the delayed result of cardiac ventricular systoles, is, however, more resistant to noise, artifacts, and distortion. Accordingly, the methods of the present invention use information and hints about the present phase of the cardiac cycle derived from the PPU signal to discriminate non-physiological, or artifactual, from physiological, or actual, information concerning cardiac phases derived from the ECG signal.

FIG. 3 illustrates exemplary signals 30 of the present invention. For ease of description only, illustrated are approximately one second of signals that could occur in a generally healthy patient with a heart rate of about 60/sec., the ECG signal being illustrated as free of artifacts. The illustrated, exemplary, scalar ECG, including two complete complexes 31 and 32, is that typically obtained from lead 1, other leads resulting in other well-known forms of the scalar ECG signal that can equally well be utilized alone or in combination in the present invention. Various phases of cardiac motion can be recognized in the ECG signal and used to control imaging data collection. For example, atrial systole can be recognized as starting at the beginning of the P-wave, which represents atrial depolarization, and extending approximately to the beginning of the QRS complex, thereby having a duration approximated by the P–R interval. Ventricular systole can be recognized as beginning at the start of the QRS complex, which represents ventricular depolarization, and extending to the end of the T-wave, which represents ventricular repolarization, thereby having a duration approximated by the Q–T interval. Finally, cardiac diastole can be recognized as extending from the end of one T-wave to the beginning of the next successive P-wave. The durations of the various waves and of the intervals between the waves have well-known and tabulated values varying by age, sex, heart rate, disease state, and so forth.

Figure 2B:
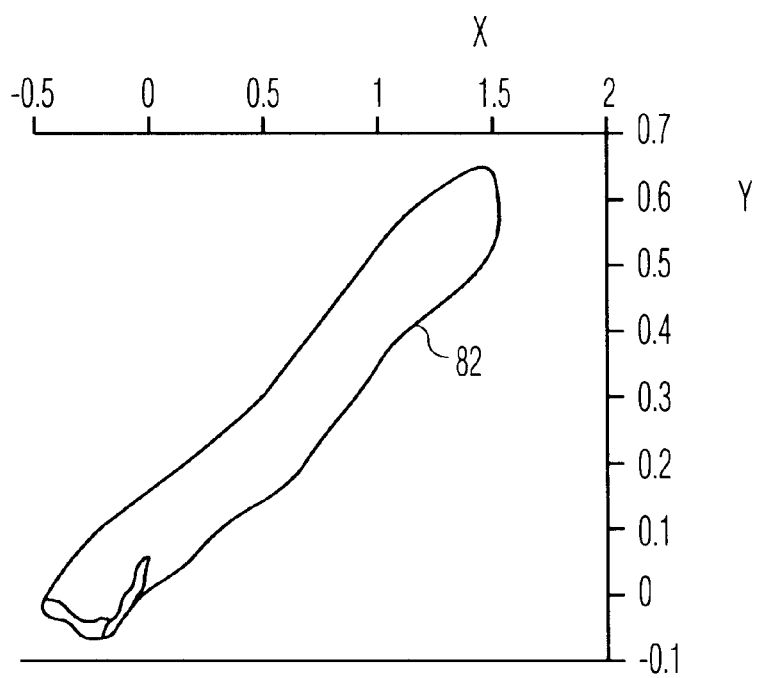
FIG. 2B illustrates an exemplary vector ECG signal.

Although primarily described for simplicity with respect to scalar ECG signals, the present invention is equally adaptable to use of vector ECG (VCG) signals. VCG signals are taken herein to signify a record of the simultaneous time course of two or more voltages defining a projection of the cardiac net depolarization vector. For example, loop 82 in FIG. 2B illustrates a frontal projection of the time course of the tip cardiac depolarization vector during a normal QRS complex, other waves of the ECG being represented by other loops of less amplitude. The VCG, like the ECG, can be disturbed by noise and artifacts when recording during a medical imaging experiment. In this invention, use of the VCG merely involves replacing the recognition of the waves and complexes of the scalar ECG with the recognition of the corresponding loops of the VCG. VCG recognition can be done by known means.

Depending on the medical goals of a particular imaging examination, imaging data collection can be synchronized with, or limited to, both easily recognized cardiac phases as well as with other phases of the cardiac cycle. Since the R-wave is often the most easily recognizable component of an ECG signal, imaging data collection is often preferably synchronized with R-waves. Although, for ease of description, the following discussion is generally directed to such R-wave synchronization, one of skill in the art will understand how to apply the present invention to synchronize imaging data collection with any other feature of the ECG signal and with any phase of the cardiac cycle. This invention encompasses such general synchronizations.

The PPU signal illustrated in FIG. 3, including two bilobate PPU complexes 33 and 34, is exemplary of that obtained from a patient's finger. The positive lobes the PPU complexes indicate systolic arterial and capillary blood flow away from the heart. Typically, the start of the positive PPU lobe is delayed approximately by 150 msec. (typical range 50–200 msec.) from the R-wave, which marks the start of ventricular systole, and has a duration of approximately 300 msec. (typical range 200–400 msec.).

According to the methods of the present invention, information derived from PPU signals, represented by relation 35, is used to guide and assist recognition of determined phases of the cardiac cycle from features recognized in the ECG signal in order that synchronization signals for a medical imaging apparatus can be derived, as represented by relations 36, with increased reliability. Generally, PPU signals can be used either to establish "black-outs", intervals during which a true, or physiological, R-wave cannot occur or is improbable (for example, less than 10%), or to establish "windows", intervals during which true R-waves occur or are probable (for example, greater than 90%). Black-outs recognized during ventricular systole are advantageous since hydrodynamic effects during systole often introduce large and confusing artifacts into the ECG signal. In FIG. 3, black-outs are represented by striped intervals, such as black-out 37, while windows are represented by open intervals, such as window 41.

In more detail, black-outs can be recognized with reference to only a single PPU complex. For example, no true, or physiologic, R-waves can occur during systole, the time of peripheral systolic blood flow due to the previous R-wave. Therefore, the positive lobes of PPU complexes 33 and 34, intervals 37 and 37', respectively, which indicate peripheral systolic blood flow, are black-outs.

Also black-outs can be recognized with reference to two or more PPU complexes, information from a previous PPU complex being used to expand the duration of the black-out associated with the following PPU complex. For example, the delay between the end of the next following QRS-complex and the end of the positive lobe of the just previous PPU complex can be observed for an individual patient, and then used to establish a black-out, which begins at or just after the predicted start of the QRS-complex, as determined by adding the observed delay to the time of the end of the just previous PPU complex, and which ends at the end of the positive lobe of the following PPU complex. Accordingly, black-out 39 begins at a time delayed by delay 38 from the end of the positive lobe of PPU complex 33 and ends at the end of the positive lobe of PPU complex 34.

A window for the next physiologic R-wave can be predicted by reference to the previous PPU complex, optionally combined with reference to the previous QRS complex. For example, the delay between the start of the next QRS-complex and the end of the positive lobe of the previous PPU complex can also be observed for a particular patient, and then used to establish an R-wave window, which begins at or just before the start of the QRS-complex determined by adding the delay to the ending time of the previous PPU complex, and which ends at the beginning of the positive lobe of the next PPU complex following ventricular systole. Accordingly, window 41 begins at a time delayed by delay 40 from the end of the positive lobe of PPU complex 33 and ends at the start of the positive lobe of PPU complex 34. Alternately, window 41 can end after a further observed or reference delay defining an interval during which the next physiologic QRS-complex should have occurred.

The delay values used above can be measured in known manners from a particular patient in a particular medical imaging apparatus prior to image data acquisition. During imaging, the various delay values can be updated by, for example, maintaining the delay values as running averages. Alternatively, the various delay values used, or initial delay values to be updated, can be obtained from tables of expected delay values depending on the age, sex, heart rate, condition, and so forth of the patient.

In further embodiments, windows, black-outs and other PPU-derived information useful to assist and guide ECG feature recognition can be derived from a current PPU complex, optionally combined with one or more prior PPU complexes and with information from ECG signals, as will be apparent to one of skill in the art in view of the description above. The present invention includes such apparent variations.

PPU-derived information can be used to assist and guide ECG feature recognition in known manners. For example, ECG feature recognition can be guided by, or be responsive to, the probability of the feature occurring. In improbable black-outs, the feature must be very clearly present to be detected, while in windows, its presence can be less certainly present in order to be detected. For a further example, during black-outs, scanning input ECG signals to recognize features, such as R-waves, can be completely suppressed. Alternately, feature scanning can be enabled only during windows.

Finally, according to the present invention, synchronization signals for controlling imaging data collection are derived from ECG features recognized with the guidance and assistance from PPU-derived information. For example, synchronization signals 42 and 43 are generated promptly upon recognition of the R-waves in ECG complexes 31 and 32, and are promptly output to the control unit of the medical imaging apparatus. This timing is advantageous to image the heart in systole. Alternately, synchronization signals can be generated and output in a pre-determined temporal relationship to, such as a delay from, detected R-waves. For example, signals 42' and 43' are delayed by the duration of the Q-T interval, the length of ventricular systole, so that imaging data collection starts at the beginning of cardiac diastole. This timing is advantageous to generally minimize artifacts due to cardiac motion and to flowing blood. Of course, synchronization signals can be generated in other temporal relations to detected R-waves, or other recognized features of the cardiac cycle.

Alternatively, in addition to synchronization signals initiating imaging data collection, further types of synchronization signals can be generated. Depending on the predetermined delay of a synchronization signal from a detected cardiac event, for example, a delay from a detected R-wave, and also depending on the nature of the additional information derived from the PPU complex, a previously "detected" event may later be discovered to be non-physiologic, or an artifact. In this case, an additional synchronization signal can be generated indicating that the prior synchronization signal represented, in fact, a non-physiologic artifact. Imaging data collected in response to the first synchronization signal can be then discarded or marked to be ignored during image reconstruction. Of course, the faulty data must be collected again. Alternatively, verification-type synchronization signals can always be generated at the end of a cardiac cycle in view of all accumulated ECG and PPU information, a positive verification indicating that the collected imaging data is good while a negative verification indicating that due to an artifact the collected imaging data should discarded.

A minimum number of negative verification signals is preferable because discarded imaging data must be collected again. The time of a medical imaging examination is thereby lengthened.

Finally, with respect to FIG. 4, the final steps of the methods of the present invention are described in a preferred embodiment applied to MR imaging. For other imaging modalities, in response to the synchronization signals, the control unit of the medical imaging apparatus would generate control signals appropriate to the particular imaging apparatus. Turning to FIG. 4, in which illustrated elements also appearing in FIG. 3 have the same reference numbers, illustrated therein are signals 50, including ECG signals with ECG complexes 31 and 32, and synchronization signals 42' and 43', which are displaced from the detected R-waves of complexes 31 and 32 to the beginning of the following cardiac diastole. PPU signals and PPU-derived information are omitted from FIG. 4 for simplicity. Also illustrated are MR signals generated by an MR apparatus triggered by the illustrated synchronization signals. Thus, MR signals 52 are triggered 54 by synchronization signal 42' indicating the beginning of the diastole following ECG complex 31. Partially illustrated are MR signals 51 collecting during the previous diastole, and MR signals 53 triggered by synchronization signal 43' during the following diastole.

Any appropriate MR protocol may be triggered by the synchronization signals of this invention. For appropriate MR protocols generally, see Vlaardingerbroek et al., 1996, *Magnetic Resonance Imaging: Theory and Practice*, Springer-Verlag; Stark et al., 1992, *Magnetic Resonance Imaging*, Mosby.

In detail, magnetic resonance signals 55 illustrate an exemplary fast, slab-selective, 3D, gradient echo pulse sequence with spoiling but no gradient moment nulling and typically using flip angles, $\alpha$, of between 15° and 30°. Data collections are triggered during diastole when the heart assumes its greatest size and blood flow velocities are smallest. Preferably, during each diastole all the phase encode lines for one slice are collected by varying the phase-encode magnetic field gradients, $G_{PHASE}$, as illustrated. Preferably data for successive 3D slices are acquired during successive diastoles by varying the slice-encode magnetic field gradient, $G_{SLICE}$, as illustrated. MR signals are received during the read magnetic gradient field, $G_{READ}$. A 3D examination is completed by sufficient repetitions of this sequence.

It is to be understood that MR signals 55 are exemplary and presented for definiteness of description. Other MR data collection protocols appropriate to different diagnostic needs can be triggered by the synchronization signals of the present invention.

Implementations of the Methods the Present Invention

Figure 5:
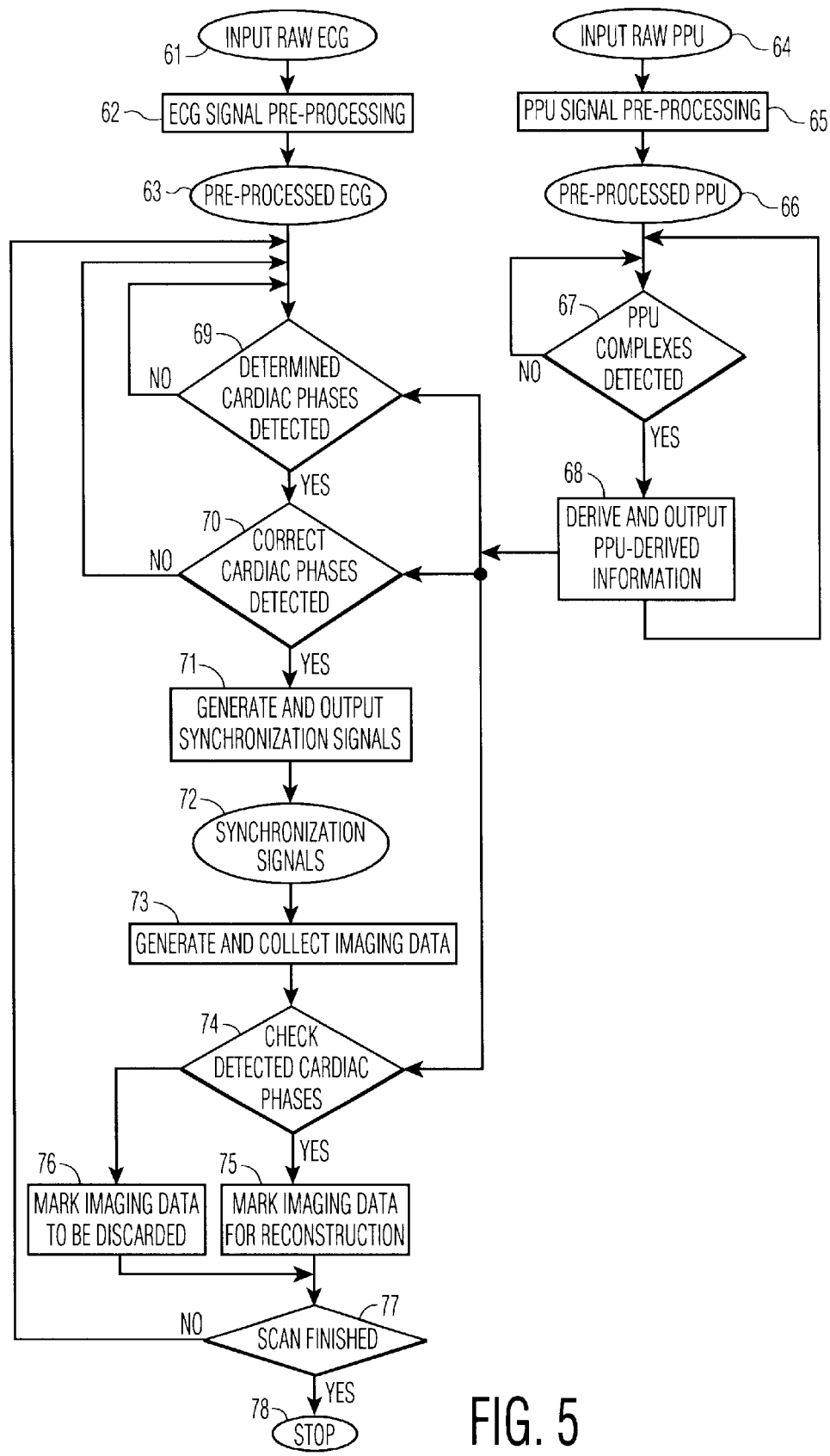
FIG. 5 illustrates an exemplary implementation of the methods of the present invention.

Lastly, exemplary hardware and software implementations of the methods of the present invention are described. Turning to FIG. 5, the exemplary software implementation illustrated therein is structured as two cooperating processes, an ECG-Process for processing ECG signals and a PPU-Process for processing PPU signals. These processes cooperate by exchanging information, represented by arrows 60, using techniques known to those of skill in the art, for example, signals can be sent between the two processes, shared data variables can be updated by the two processes, or so forth.

Inputs to both processes include their respective pre-processed signals, pre-processed ECG signals 63 for the ECG-Process and pre-processed PPU signals 66 for the PPU-Process. In detail, for the ECG-Process, pre-processing step 60 inputs raw ECG signals from patient electrodes 15 (FIG. 1) to signal pre-processing step 61 typically implemented in ECG unit 14 (FIGS. 1A and 1B). Signal pre-processing typically high-pass filters the analog input signal, digitizes it, removes from the digitized signal obvious or simple artifacts, such as spikes or baseline drift, and makes the pre-processed ECG signals available in real-time. Similarly for the PPU-Process, pre-processing step 64 inputs raw PPU signals from patient pulse sensor 16 (FIGS. 1A and 1B) to signal pre-processing step 63 typically implemented in PPU unit 17 (FIG. 1). PPU pre-processing step 65 preferably performs actions similar to those performed by ECG pre-processing step 62.

The remaining steps, in the exemplary software embodiment, are typically implemented in synchronization unit 18 (FIGS. 1A and 1B), which receives the digitized ECG and PPU input signals in real time. Turning first to the PPU process, in the loop at step 67, the synchronization unit first searches for and recognizes bilobate PPU complexes in the pre-processed PPU input. The start of a PPU complex can be recognized, for example, when the PPU input sufficiently deviates from baseline, and its presence can be confirmed by, for example, cross-correlation with a reference PPU complex or a previously measured actual PPU complex. However, this invention is adaptable to known recognition methods, such as those based on signal processing, artificial intelligence, or fuzzy logic principles. See generally Todd, 1999, The identification of peaks in physiological signals, *Computational Biomedical Research* 32:322–35. Once recognized, features of the bilobate PPU complexes, especially their timing, are used in the above-described methods of the present invention to generate PPU-derived information, such as black-outs, windows, negative verifications, or so forth. Output from step 68 is continuously updated PPU-derived information made available to the ECG-Process as indicated by arrows 60.

Turning next to the ECG-Process, in the loop at step 69, the synchronization unit searches for and recognizes pre-determined phases of cardiac motion represented by certain pre-determined ECG signal characteristics. For example, step 69 searches for the presence of R-waves in the ECG signal by recognizing their characteristic peaks. As represented by arrows 60, this step is guided by PPU-derived information, for example, by searching the input ECG signal only in PPU-determined temporal windows. ECG recognition methods are well known in the art, and this invention can employ the variously known recognition methods, such as those based on signal processing, artificial intelligence, or fuzzy logic principles. Next, the loop at step 70 checks the correctness of the detected cardiac phase in view of further PPU-derived information also input from step 68 of the PPU-Process. For example, the detection of a cardiac phase during a PPU-derived black-out for that phase can be suppressed in this step. Output from steps 69 and 70 is a time series of detected pre-determined types of cardiac phases, the detection making use of PPU-derived information to guide detection from the ECG signal.

Next, the synchronization unit at step 71 generates and outputs the actual physical synchronization signals from the series of detected cardiac phases. For example, a synchronization signal can be generated after each R-wave with a sufficient delay for it to mark the expected beginning of diastole. Synchronization signals 72 are then presented to the MR control unit 11 (FIG. 1A) or to CT control unit 29 (FIG. 1B) in order to trigger collection of the appropriate medical imaging data at step 73. In the case of other modalities, synchronization signals are appropriately presented to control imaging data acquisition.

As described above, information derived from succeeding members of the series of detected cardiac phases and detected PPU complexes may indicate that a previously generated synchronization signal is, in fact, associated with a non-physiologic cardiac phase. In that case, a negative verification signal is generated to suppress the use of image data collected in response to a non-physiologic synchronization signal. Accordingly, the synchronization unit at step 74 checks the previously detected cardiac phases using current information from the determined cardiac phases and using current PPU-derived information, as represented by arrows 60. If the previous synchronization signal was correctly detected, collected imaging data is marked for use in medical image reconstruction at step 75, otherwise it is marked to be discarded at step 76.

Finally, steps 77 and 78 iterate the above ECG-Process until all imaging data necessary for image reconstruction have been correctly collected.

The ECG-Process and the PPU-Process preferably performed in units 14, 17 and 18 (FIGS. 1A and 1B) can, in one embodiment, be implemented with dedicated electronic components in fixed circuit arrangements. Preferably, however, the processing steps are implemented instead with programmable elements, such as one or more programmable signal processors or microprocessors, communicating over busses with support RAM, ROM, analog signal interfaces, and so forth. In the preferable implementation, the programmable elements are commanded to perform the above-described steps with software modules loaded into RAM or ROM. Such software can be written according to well-known methods to perform the real-time processing required herein.

Further, units 14, 17 and 18 can be provided with one or more storage interfaces so that these software modules can be loaded in the RAM or ROM from computer-readable media. Also, units 14, 17, and 18 can be implemented physically as separate units or variously combined into one or two units or with MR control unit 11 (FIG. 1A), or with CT control unit (FIG. 1B), or with the control unit or controller of other medical imaging modalities.

One of skill in the art, in view of the above description, will recognize equivalent hardware and software implementations for performing the methods of this inventions. It is intended that the appended claim encompass such recognized equivalent implementations.

All references cited herein are incorporated herein by reference in their entirety and for all purposes to the same extent as if each individual publication or patent or patent application was specifically and individually indicated to be incorporated by reference in its entirety for all purposes.

What is claimed is:

1. A method of medical imaging comprising:
    obtaining electrocardiogram (ECG) signals representing the electrocardiogram of a patient placed in an examination zone of a medical imaging apparatus which collects medical imaging data for reconstruction of a medical image,
    obtaining peripheral pulse (PPU) signals representing occurrences of peripheral pulses in the patient,
    providing one or more synchronization signals representing occurrences of one or more pre-determined phases of the cyclic movements of the heart, wherein the synchronization signals are provided in dependence on both the ECG signals and on the PPU signals, and
    controlling the medical imaging apparatus in dependence on the one or more synchronization signals to collect imaging data synchronized with cyclic movements of the heart from a part of the patient in the examination zone and to reconstruct a medical image of the part of the patient from the collected imaging data.

2. The method of claim 1 wherein the part of the patient includes cardiac structures, or intracranial structures, or vascular structures.

3. The method of claim 1 wherein the medical imaging apparatus includes a magnetic resonance apparatus or a computed tomography x-ray apparatus.

4. The method of claim 1 wherein the step of obtaining ECG signals further comprises obtaining scalar ECG signals or obtaining vector ECG signals.

5. The method of claim 1 wherein the synchronization signals are provided only if the PPU signals indicate that the pre-determined cardiac phases are physiologically possible.

6. The method of claim 1 wherein the step of providing further comprises:
   determining, first, PPU-derived information from the PPU signals, wherein the PPU-derived information indicates time intervals within which the pre-determined cardiac phases are physiologically more probable or less probable, and
   recognizing, second, the pre-determined cardiac phases in the ECG signal, wherein the recognizing is responsive to the probability or improbability of the pre-determined cardiac phases indicated by the PPU-derived information.

7. The method of claim 6 wherein the PPU-derived information indicates black-out intervals within which the pre-determined cardiac phases cannot occur, and wherein the pre-determined cardiac phases are not recognized during black-out intervals.

8. The method of claim 6 wherein the PPU-derived information indicates window intervals only within which the pre-determined cardiac phases can occur, and wherein the pre-determined cardiac phases are recognized only during window intervals.

9. The method of claim 1 wherein the provided synchronization signals further comprise verification-type signals which indicate whether or not a previous synchronization signal represents a physiologic cardiac phase, and wherein the medical imaging apparatus is controlled to not use for image reconstruction imaging data collected in response to non-physiologic synchronization signals.

10. The method of claim 1 wherein the step of providing provides R-wave-type synchronization signals that signal occurrences of R-waves in the ECG signals, and wherein the step of controlling collects imaging data in a pre-determined temporal relation to R-wave-type signals.

11. The method of claim 10 wherein the pre-determined temporal relation is such that imaging data is collected during cardiac diastole.

12. The method of claim 10 wherein the step of providing further comprises determining from the PPU signal black-out intervals within which physiologic R-waves cannot occur in the ECG signals, and wherein R-wave-type synchronization signals are not provided during black-out intervals.

13. The method of claim 12 wherein the PPU signal comprises PPU complexes having positive lobes indicating peripheral systolic blood flow, and wherein black-out intervals comprise the duration of the positive lobes of PPU complexes.

14. The method of claim 10 wherein the step of providing further comprises determining from the PPU signal window intervals within which physiologic R-waves in the ECG signal must occur, and wherein R-wave-type synchronization signals are provided only during window intervals.

15. The method of claim 14 wherein the PPU signal comprises PPU complexes having positive lobes indicating peripheral systolic blood flow, and wherein each window interval comprises an interval which begins at a pre-determined duration after the end of a just previous QRS complex in the ECG signal, and which ends at the beginning of the positive lobe of an immediately next PPU complex.

16. A magnetic resonance (MR) apparatus for acquiring images of a part of a patient placed in an examination zone of the MR apparatus, the apparatus comprising:

a main magnet system for generating a steady magnetic field in the examination zone, a gradient magnet system for generating temporary gradient magnetic fields in the examination zone, a radio frequency (RF) transmitter system for generating RF pulses in the examination zone, an RF receiver system for receiving MR signals from the examination zone, an electrocardiogram (ECG) system for obtaining ECG signals representing the electrocardiogram of the patient, a peripheral pulse unit system for obtaining peripheral pulse (PPU) signals representing occurrences of peripheral pulses in the patient, a reconstruction unit for reconstructing an image of the region of the patient from the received MR signals, a control unit responsive to one or more synchronization signals for generating control signals controlling the gradient magnet system, the RF transmitter system, the RF receiver system, and the reconstruction unit, wherein the synchronization signals represent occurrences of one or more pre-determined phases of the cyclic movements of the heart, and wherein the control signals cause acquisition of MR data for the reconstruction an image of a part of the patient, and a synchronization unit for providing the one or more synchronization in dependence on both the ECG signals and on the PPU signals in order to synchronize the acquisition of MR signals with cyclic movements of the heart.

17. The system of claim 16 wherein the synchronization unit further comprises:
   means for determining, first, PPU-derived information from the PPU signals, wherein the PPU-derived information indicates time intervals within which the pre-determined cardiac phases are physiologically more probable or less probable, and
   means for recognizing, second, the pre-determined cardiac phases in the ECG signals, wherein the recognizing is responsive to the probability or improbability of the pre-determined cardiac phase indicated by the PPU-derived information.

18. The system of claim 16 wherein the synchronization unit further comprises:
   one or more programmable elements, and
   one or more memories for storing instructions for causing the synchronization unit to function for providing the synchronization signals in dependence on both the ECG signals and on the PPU signals in order to synchronize the acquisition of MR signals with cyclic movements of the heart.

19. A computed tomography (CT) x-ray apparatus for acquiring images of a part of a patient placed in an examination zone of the CT apparatus, the apparatus comprising:

a radiation source, a detector unit which is coupled to the radiation source means for causing the radiation source and the detector unit to perform a rotational scanning motion about the patient in the examination zone during which scanning motion measuring data is acquired, an electrocardiogram (ECG) system for obtaining ECG signals representing the electrocardiogram of the patient, a peripheral pulse unit system for obtaining peripheral pulse (PPU) signals representing occurrences of peripheral pulses in the patient, a reconstruction unit for reconstructing the spatial distribution of the absorption within the patient from the measuring data acquired by the detector unit, and a control unit responsive to one or more synchronization signals for generating control signals controlling the radiation source, the detector unit, the means for causing a rotational scan, and the reconstruction unit, wherein the synchronization signals represent occurrences of one or more pre-determined phases of the cyclic movements of the heart, and wherein the control signals cause acquisition of measuring data for the reconstruction an image of a part of the patient, and a synchronization unit for providing the one or more synchronization signals in dependence on both the ECG signals and on the PPU signals in order to synchronize the acquisition of measuring data with cyclic movements of the heart.

20. A computer readable media carrying encoded program instructions for causing a medical imaging apparatus to perform the method of claim 1.

* * * * *

UNITED STATES PATENT AND TRADEMARK OFFICE
CERTIFICATE OF CORRECTION

PATENT NO.     : 6,501,979 B1                                                         Page 1 of 1
DATED          : December 31, 2002
INVENTOR(S)    : Warren J. Manning, Rene M. Botnar and Matthias Stuber It is certified that error appears in the above-identified patent and that said Letters Patent is hereby corrected as shown below:

<u>Title page,</u>
Item [73], Assignee, insert -- and Beth Israel Deaconess Medical Center Corporation, Boston, MA --.

Signed and Sealed this

Twelfth Day of August, 2003

JAMES E. ROGAN
*Director of the United States Patent and Trademark Office*